(12) United States Patent
Rigler (10) Patent No.: US 7,754,427 B2
(45) Date of Patent: Jul. 13, 2010

(54) PARALLEL HIGH THROUGHPUT SINGLE MOLECULE SEQUENCING PROCESS

(76) Inventor: Rudolf Rigler, 115, rue du Centre, 1025 St-Sulpice (CH)

( * ) Notice: Subject to any disclaimer, the term of this patent is extended or adjusted under 35 U.S.C. 154(b) by 557 days.

(21) Appl. No.: 11/628,400

(22) PCT Filed: Aug. 5, 2005

(86) PCT No.: PCT/EP2005/008511

§ 371 (c)(1),
(2), (4) Date: Nov. 30, 2006

(87) PCT Pub. No.: WO2006/013110

PCT Pub. Date: Feb. 9, 2006

(65) Prior Publication Data

US 2007/0248966 A1    Oct. 25, 2007

Related U.S. Application Data

(60) Provisional application No. 60/662,798, filed on Mar. 18, 2005.

(30) Foreign Application Priority Data

Aug. 6, 2004   (DE) .................. 10 2004 038 359

(51) Int. Cl.
*C12Q 1/68* (2006.01)
*C12M 1/40* (2006.01)
(52) U.S. Cl. .................. 435/6; 435/174; 435/287.1; 435/287.2
(58) Field of Classification Search .................. None
See application file for complete search history.

(56) References Cited

U.S. PATENT DOCUMENTS 6,210,896 B1    4/2001   Chan
2005/0130159 A1  6/2005   Rigler et al.

FOREIGN PATENT DOCUMENTS

| WO | WO-00/70073 A | 11/2000 |
|---|---|---|
| WO | WO-01/16375 A | 3/2001 |
| WO | WO-03/052136 A | 6/2003 |
| WO | WO-03/052137 A | 6/2003 |

*Primary Examiner*—James Martinell
(74) *Attorney, Agent, or Firm*—Fulbright & Jaworski LLP (57) ABSTRACT

The invention relates to a process and to an apparatus for parallel high throughput sequencing of nucleic acid molecules, in particular in the single molecule format. The present invention further relates to a process and an apparatus for a parallel high throughput study of enzyme-substrate interactions, in particular in the single molecule format.

24 Claims, 5 Drawing Sheets

PARALLEL HIGH THROUGHPUT SINGLE MOLECULE SEQUENCING PROCESS

This is a §371 of PCT/EP2005/008511 filed Aug. 5, 2005, which claims priority from German Patent Application No. 10 2004 038 359.6 filed Aug. 6, 2004 and U.S. Ser. No. 60/662,798 filed Mar. 18, 2005.

The invention relates to a process and to an apparatus for parallel high throughput sequencing of nucleic acid molecules, in particular in the single molecule format. The present invention further relates to a process and an apparatus for a parallel high throughput study of enzyme-substrate interactions, in particular in the single molecule format.

Sequencing of the human genome which consists of approx. $3 \times 10^9$ bases, or of the genome of other organisms and the determination and comparison of individual sequence variants requires the provision of sequencing methods which firstly are fast and secondly can be employed routinely and cost-effectively. Although large efforts have been made in order to accelerate familiar sequencing methods, for example the enzymic chain termination method according to Sanger et al. (Proc. Natl. Acad. Sci. USA 74 (1977) 5463), in particular by automation (Adams et al., Automated DNA Sequencing and Analysis (1994), New York, Academic Press), currently only up to 2000 bases per day can be determined using an automated sequencer.

Over recent years, new approaches to overcome the limitations of conventional sequencing methods have been developed, inter alia sequencing by scanning tunneling microscopy (Lindsay and Phillip, Gen. Anal. Tech Appl. 8 (1991), 8-13), by highly parallel capillary electrophoresis (Huang et al., Anal. Chem. 64 (1992), 2149-2154; Kambara and Takahashi, Nature 361 (1993), 565-566), by oligonucleotide hybridization (Drmanac et al., Genomics 4 (1989), 114-128; Khrapko et al., FEBS Let. 256 (1989), 118-122; Maskos and Southern, Nucleic Acids Res. 20 (1992), 1675-1678 and 1679-1684) and by matrix-assisted laser desorption/ionization mass spectroscopy (Hillenkamp et al., Anal. Chem. 63 (1991), 1193A-1203A).

Another approach is single-molecule sequencing (Dörre et al., Bioimaging 5 (1997), 139-152), in which the sequence of nucleic acids is carried out by progressive enzymic degradation of fluorescently labeled single-stranded DNA molecules and by detection of the sequentially released monomeric molecules in a microstructure channel. This process has the advantage of only a single molecule of the target nucleic acid being sufficient for carrying out a sequence determination.

Although application of the abovementioned methods has already resulted in considerable progress, there is a great need for further improvements. The object on which the present invention is based was therefore to provide a process for sequencing nucleic acids, which represents a further improvement compared to the prior art and which makes possible parallel determination of individual nucleic acid molecules in a multiplex format.

PCT/EP01/07462 proposes a multiplex sequencing process which comprises providing, in an immobilized form, nucleic acid molecules carrying a plurality of fluorescent labeling groups on a support and determining simultaneously the base sequence of a plurality of nucleic acid molecules on the basis of the time-dependent change, caused when nucleotide building blocks are cleaved off, in the fluorescence of said nucleic acid molecules or/and said cleaved-off nucleotide building blocks. According to WO 2003/052137, the sequence is determined by irradiating light into the support and generating an evanescent excitation field by way of internal reflection on the support surface in the region of the immobilized nucleic acid molecules.

The present application relates to a process for sequencing nucleic acids, comprising the following steps:
(a) providing a support having a multiplicity of nucleic acid-degrading enzyme molecules immobilized thereon,
(b) contacting said support with free nucleic acid molecules carrying a plurality of fluorescent labeling groups,
(c) progressively cleaving off individual nucleotide building blocks from said free nucleic acid molecules by said immobilized enzyme molecules, and
(d) simultaneously determining the base sequence of a plurality of nucleic acid molecules on the basis of the time-dependent change, caused when nucleotide building blocks are cleaved off, in the fluorescence of said nucleic acid molecules or/and of said cleaved-off nucleotide building blocks.

The process of the invention is a support-based multiplex sequencing method which enables a multiplicity of individual free nucleic acid molecules to be studied in parallel. This is achieved by providing a support having a plurality of nucleic acid-degrading enzyme molecules immobilized thereon and determining in parallel the fluorescence of a plurality of degradation reactions. The process is preferably carried out in the form of a parallel high throughput single molecule analysis.

The support used for said process may be any planar or structured support which is suitable for immobilizing enzyme molecules. Examples of suitable support materials are glass, quartz, plastic, metals, semimetals such as silicon, for example, metal oxides such as silicon dioxide, for example, or composites comprising said materials. Said support may, at least in the region of the immobilized enzyme molecules, have sufficient optical transparency and suitable surface properties for irradiation with fluorescence excitation light or/and backscatter of fluorescence emission light through the support or for evanescence-based fluorescence detection. In principle, the support may also have any design, as long as a reaction space can be formed which enables individual nucleotide building blocks to be cleaved off progressively from the nucleic acids contacted with said support in a liquid reaction mixture.

The enzyme molecules may bind to this support via covalent or noncovalent interactions. For example, high-affinity interactions between the partners of a specific binding pair, for example biotin/streptavidin or avidin, haptene/anti-haptene antibody, sugar/lectin, etc., can mediate binding of the polypeptides to the support. Thus it is possible to couple biotinylated enzyme molecules to streptavidin-coated supports. Alternatively, the enzyme molecules may also be bound to the support via adsorption. Thus enzyme molecules modified by incorporation of alkane thiol groups, may bind to metallic supports, e.g. supports made of gold. Yet another alternative is covalent immobilization in which it is possible to mediate enzyme molecule binding via reactive silane groups on a silica surface.

A plurality of enzyme molecules is bound to a single support. The enzyme molecules immobilized on the support and the sample liquid in contact therewith, which contains the nucleic acid molecules to be degraded, define one or more reaction spaces. Preferably at least 100, particularly preferably at least 1000, and particularly preferably at least 10000, and up to more than $10^6$, enzyme molecules are bound to said support. Preference is given to said enzyme molecules binding to said support in such a way that a diluted enzyme layer is produced on said support, preferably containing from 0.01 to 2, preferably 0.1 to 1, enzyme molecules per $\mu m^2$ of support surface area. The enzyme molecules may be applied randomly, for example by contacting a diluted solution of biotinylated enzyme molecules with a support two-dimensionally coated with streptavidin. Alternatively, the enzyme molecules may also be bound to specific regions of the support surface, for example by contacting a diluted solution of biotinylated enzyme molecules with a structured support, only particular regions of which are coated with streptavidin. The nucleic acid molecules to be sequenced may be in single-stranded or in double-stranded form. They are preferably from 50 to 2000 nucleotides, particularly preferably from 200 to 1000 nucleotides, in length. The nucleic acid molecules to be sequenced, for example DNA molecules or RNA molecules, contain a plurality of fluorescent labeling groups, with preferably at least 50%, particularly preferably at least 70%, and most preferably essentially all, for example at least 90%, of the nucleotide building blocks of one or more, for example two, three or four, base types carrying a fluorescent labeling group, each base type favorably carrying a different fluorescent labeling group. It is not necessary to label completely all nucleotide building blocks of a single base type, since it is possible, when determining the sequence of a single nucleic acid molecule, to fill in possible gaps by multiple parallel determinations.

Nucleic acids labeled in this way may be generated by enzymic primer extension on a nucleic acid template by using a suitable polymerase, for example a DNA polymerase such as, for example, Taq polymerase, a thermostable DNA polymerase from Thermococcus gorgonarius or other thermostable organisms (Hopfner et al., PNAS USA 96 (1999), 3600-3605), or a mutated Taq polymerase (Patel and Loeb, PNAS USA 97 (2000), 5095-5100), by using fluorescently labeled nucleotide building blocks. Preference is given to polymerases without exonuclease activity, such as Vent exo- or Tgo exo, for example. Particularly preferred methods for incorporating fluorescent labeling groups are described in Tasara et al. (Nucleic Acids Res. 31 (2003), 2636-2646) or Giller et al. (Nucleic Acids Res. 31 (2003), 2630-2635).

It is also possible to prepare the labeled nucleic acid molecules by amplification reactions, for example PCR. Thus an asymmetric PCR produces amplification products in which only one strand contains fluorescent labels. Such asymmetric amplification products can be sequenced in double-stranded form. Symmetric PCR produces nucleic acid fragments in which both strands are fluorescently labeled. These two fluorescently labeled strands can be separated and contacted separately in single-stranded form with the immobilized enzyme molecules so that it is possible to determine the sequence of one or both complementary strands separately. Alternatively, one of the two strands can be modified on the 3' end, for example by incorporating a PNA link, such that monomeric building blocks can no longer be removed by cleavage. In this case, double-strand sequencing is possible.

Preferably, essentially all nucleotide building blocks of at least two base types, for example two, three or four base types, carry a fluorescent label, each base type conveniently carrying a different fluorescent labeling group. If the nucleic acid molecules have not been labeled completely, it is nevertheless possible to determine the sequence completely by parallel sequencing of a plurality of molecules.

The nucleic acid template whose sequence is to be determined may be selected, for example, from DNA templates such as genomic DNA fragments, cDNA molecules, plasmids, etc., or else from RNA templates such as mRNA molecules.

The fluorescent labeling groups may be selected from known fluorescent labeling groups used for labeling biopolymers, for example nucleic acids, such as, for example, fluoresceins, rhodamines, oxazines, for example Evoblue or Gnothis Blue, pycoerythrin, Cy3, Cy5, IR dyes or derivatives thereof, etc.

The method of the invention is based on fluorescent labeling groups incorporated in nucleic acid strands interacting with neighboring groups, for example with chemical groups of the nucleic acids, in particular nucleobases such as, for example, G, or/and neighboring fluorescent labeling groups, and these interactions leading to a change in fluorescence, in particular in fluorescence intensity, compared to the fluorescent labeling groups in "isolated" form, owing to quenching processes or/and energy transfer processes. The removal by cleavage of individual nucleotide building blocks alters the overall fluorescence, for example the fluorescence intensity of an immobilized nucleic acid strand, and this change is a function of the removal by cleavage of individual nucleotide building blocks, i.e. a function of time. This time-dependent change in fluorescence may be recorded in parallel for a multiplicity of nucleic acid molecules and correlated with the base sequence of the individual nucleic acid strands. Preference is given to using those fluorescent labeling groups which, when incorporated in the nucleic acid strand, are, at least partially, quenched so that the fluorescence intensity is increased after the nucleotide building block containing the labeling group or a neighboring building block causing quenching has been removed by cleavage.

The sequencing reaction of the process of the invention comprises progressively cleaving off individual nucleotide building blocks from the nucleic acid molecules to be sequenced by immobilized, nucleic acid-degrading enzyme molecules. Preference is given to using as enzyme molecules exonucleases, it being possible to use single-strand or double-strand exonucleases which degrade in the 5'→-3' direction or 3'→-5' direction. Exonucleases which are particularly preferably used are T7 DNA polymerase, E.coli exonuclease I and E.coli exonuclease III.

During the progressive removal by cleavage of individual nucleotide building blocks, it is possible to measure a change in fluorescence intensity of the nucleic acid strand or/and the cleaved-off nucleotide building block, owing to quenching processes or energy transfer processes. This change in fluorescence intensity with time depends on the base sequence of the nucleic acid strand studied and can therefore be correlated with the sequence. The complete sequence of a nucleic acid strand is usually determined by generating, preferably by enzymic primer extension as described above, and sequencing a plurality of nucleic acid strands, labeled on different bases, for example A, G, C and T, or combinations of two different bases. It is possible, where appropriate, to attach to the nucleic acid strand to be studied also a "sequence identifier", i.e. a labeled nucleic acid of known sequence, for example by enzymic reaction using ligase or/and terminal transferase, so that at the start of sequencing initially a known fluorescence pattern and only thereafter the fluorescence pattern corresponding to the unknown sequence to be studied is obtained.

In order to accelerate the removal of cleaved nucleotide building blocks from the immobilized nucleotide strands, preferably a convectional flow away from the support is generated in the reaction space. The flow rate may be in the range from 1 to 10 mm/s.

The detection comprises irradiating light into the support, preferably by means of a laser, in order to cause excitation of the fluorescent labeling groups. It is possible, in this connection, to use one or more laser beams, for example an expanded laser beam, having a cross section of approx. 1-20 mm, or/and multiple laser beams. The detection preferably comprises a multipoint fluorescence excitation by lasers, for example a dot matrix of laser dots generated via diffraction optics or a quantum well laser.

Alternatively, fluorescence may also be detected by irradiating light into the support and generating an evanescent excitation field by way of internal reflection at the support surface in the region of the immobilized enzyme molecules. Internal reflection at one or more positions of the support surface in the region of immobilized nucleic acid molecules generates an evanescent excitation field which causes excitation of the fluorescent labeling groups of the nucleic acid molecules to be sequenced. Said reflection at the support surface is preferably total internal reflection.

Fluorescence emission of a plurality of nucleic acid strands may be detected in parallel using a detector matrix which comprises, for example, an electronic detector matrix, for example a CCD camera, a CMOS detector matrix, e.g. a CMOS camera, or an avalanche photodiode matrix. The detection may be carried out in such a way that fluorescence excitation and detection are carried out in parallel on all nucleic acid strands studied. A possible alternative to this is to study in several steps in each case a portion of the nucleic acid strands. Preference is given to carrying out the detection on fluoresence light which is emitted essentially orthogonally from the support surface through the reaction space or through the support body.

The detection may be carried out, for example, by means of confocal single molecule detection, for example by fluorescence correlation spectroscopy, which involves exposing a very small, preferably confocal, volume element, for example from $0.1 \times 10^{-15}$ to $20 \times 10^{-12}$ l, to the excitation light of a laser, which light excites the receptors present in this measuring volume so that the latter emit fluorescence light, the fluorescence light emitted from said measuring volume being measured by means of a photodetector and the change in the measured emission with time being correlated with the concentration of the analyte, so that it is possible to identify, at an appropriately high dilution, individual molecules in said measuring volume. Details of the procedure and of the apparatus used for detection can be found in the disclosure of the European patent 0 679 251. The confocal determination of single molecules is furthermore described in Rigler and Mets (Soc. Photo-Opt. Instrum. Eng. 1921 (1993), 239 ff.) and Mets and Rigler (J. Fluoresc. 4 (1994) 259-264).

Alternatively or additionally, detection may also be carried out by way of time-resolved decay measurement, called "time gating", as described, for example, by Rigler et al., "Picosecond Single Photon Fluorescence Spectroscopy of Nucleic Acids", in: "Ultrafast Phenomenes", D. H. Auston, Ed., Springer 1984. Here, the fluorescent molecules are excited in a measuring volume followed by, preferably at a time interval of $\geqq 100$ ps, opening a detection interval on the photodetector. In this way it is possible to keep background signals generated by Raman effects sufficiently low so as to enable single molecules to be detected in an essentially interference-free manner.

As indicated above, the process of the present invention requires a contact of immobilized nucleic acid-degrading enzyme molecules with free nucleic acid molecules carrying plurality of fluorescent labeling groups. In a preferred embodiment of the invention, a support may be provided having a multiplicity of nucleic acid-degrading enzyme molecules and a multiplicity of nucleic acid-polymerizing enzyme molecules co-immobilized thereon. In this embodiment, the free nucleic acid molecules carrying a plurality of fluorescent labeling groups may be directly synthesized on the support, e.g. by providing a nucleic acid template molecule, e.g. a single stranded DNA or RNA molecule, to which a primer molecule is bound which can be extended by encorporating labeled nucleotide building blocks in situ on the support. By carrying out the nucleic acid polymerization under conditions of limited processivity, e.g. by chosing enzymes having limited processivity or adjusting reaction conditions leading to limited processivity, the nucleic acid template molecule and the extended primer are liberated from the immobilized polymerase molecule and will contact a co-immobilized nucleic acid-degrading enzyme, e.g. a $3' \rightarrow 5'$-exonuclease which cleaves off individual nucleotide building blocks leading to a time dependent change in the fluorescence indicated above.

In a further aspect, the invention relates to a process for studying enzyme-substrate interactions, comprising the following steps:

(a) providing a support having a multiplicity of enzyme molecules immobilized thereon,
(b) contacting said support with free substrate molecules carrying fluorescent labeling groups,
(c) reacting said substrate molecules with said immobilized enzyme molecules, and
(d) studying simultaneously the enzyme-substrate interaction of a plurality of individual enzyme or/and substrate molecules on the basis of the time-dependent change, caused during the enzymic reaction of substrate molecules, in the fluorescence of said substrate molecules or/and cleaved-off substrate parts or/and reaction products formed.

The process of the invention is a support-based multiplex examination method which enables a multiplicity of individual enzyme molecules or/and free substrate molecules to be studied in parallel. This is achieved by providing a support, as described above, having a plurality of enzyme molecules immobilized thereon and by determining the fluorescence of a plurality of enzyme molecules in parallel. The process is preferably carried out in the form of a parallel high throughput single molecule analysis.

The support used for said process corresponds to the support described in connection with the previously described sequencing method. In principle, the support may have any design, as long as it is possible to form a reaction space which enables the substrate molecules contacted with said support to be progressively reacted in a liquid reaction mixture.

The enzyme molecules may bind to the support via covalent or noncovalent interactions, as illustrated above.

In principle, the process of the invention can employ any enzymes. Examples of suitable enzymes comprise polymerases, dehydrogenases, oxidoreductases, etc. Preference is given to immobilizing on a support identical enzyme molecules, but it is also possible to immobilize different enzyme molecules, for example variants of mutagenized enzyme libraries.

As previously described, a plurality of enzyme molecules is bound to a single support. The enzyme molecules immobilized on said support and the sample fluid in contact therewith, which contains the substrate molecules, define one or more reaction spaces. The substrate molecules to be studied contain one or more fluorescent labeling groups. These mean substrates which are fluorescent themselves, substrates which result in a fluorescent product after reaction with an enzyme, or/and substrates containing a fluorescent labeling group which is not involved in the enzymic reaction.

Substrates of this kind are known from the prior art. It is possible to study one or more different substrates on a single support.

The process of the invention is based on substrate molecules into which fluorescent labeling groups have been incorporated reacting with the enzyme molecules, which reactions result in a change in fluorescence, in particular in fluorescence intensity or/and in the fluorescence wavelength, compared to the fluorescence of fluorescent labeling groups in the substrate as starting material. In the course of said enzyme-substrate interaction, the overall fluorescence, for example the fluorescence intensity of a substrate molecule, changes as a function of the progressing interaction with the enzyme, i.e. as a function of time. This fluorescence change with time may be recorded in parallel for a multiplicity of enzyme or/and substrate molecules and correlated to the enzyme-substrate interaction.

Examples of enzyme-substrate interactions which may be studied using the process of the invention are hydrolysis, polymerization, transfer of functional groups, oxidation, reduction, dehydrogenation and isomerization.

The process of the present invention makes possible the direct resolution of conformation dynamics, binding events or cleaving reactions of biological molecules, which may result, for example, in elucidating protein functions. Information at the molecular level about the system to be studied may be obtained via fluorescence signal fluctuation.

The detection is carried out as described previously in connection with the sequencing. The detection is preferably carried out by means of confocal single molecule detection.

The invention still further relates to a process for sequencing nucleic acids, comprising the following steps:
(a) providing a support having a multiplicity of nucleic acid-polymerising enzyme molecules immobilized thereon,
(b) contacting said support with (i) free nucleic acid molecules to which a primer molecule is bound and (ii) nucleotide building blocks carrying a fluorescent labeling group,
(c) incorporating said nucleotide building blocks into said primer by said immobilized enzyme molecules, and
(d) simultaneously determining the base sequence of a plurality of nucleic acid molecules on the basis of the time-dependent change, caused when nucleotide building blocks are incorporated, in the fluorescence of said extended primer molecule or/and of said nucleotide building blocks.

The support used for this process corresponds to the supports described in connection with the previously described embodiments. The binding of the enzyme molecules to the support may also be carried out as described above.

The nucleic acid-polymerising enzyme is preferably selected from DNA polymerases and RNA polymerases, particularly from polymerases capable of a template specific nucleic acid polymerization.

The enzyme molecules immobilized on the support are contacted with free nucleic acid molecules, e.g. single-stranded DNA or RNA molecules, to which a primer molecule is bound. The primer molecule is preferably a nucleic acid or nucleic acid analogue molecule having a free 3'-end which can be extended by an enzymatic reaction. Further, the presence of nucleotide building blocks carrying a fluorescent labeling group is required. Preferably, each different nucleotide building block (A, G, C, T/U) contains a different fluorescent labeling group. When a nucleotide building block is incorporated into the primer molecule, a time dependent change in the fluorescence occurs which can be detected as indicated above. Preferably, the incorporation of the nucleotide building blocks into the primer is associated with a detectable increase in the fluorescence, preferably with a transient increase in the fluorescence. For example, nucleotide building blocks may be used which carry a fluorescent labeling group on the portion of the molecule which is cleaved off when the building block is incorporated into the primer, e.g. on the γ-phosphate group, and a fluorescence quencher group on the portion of the molecule, which is incorporated into the primer, e.g. on the α-phosphate group, on the sugar and/or on the nucleobase group.

The invention still further relates to an apparatus for sequencing nucleic acids, comprising
(a) a support comprising a multiplicity of enzyme molecules immobilized thereon,
(b) means for (i) delivering free nucleic acid molecules carrying a plurality of fluorescent labeling groups to said support, or (ii) generating free nucleic acid molecules carrying a plurality of fluorescent labeling groups on said support,
(c) a reaction space for progressively cleaving off individual nucleotide building blocks from said nucleic acid molecules, and
(d) means for determining simultaneously the base sequence of a plurality of nucleic acid molecules on the basis of the time-dependent change, caused when nucleotide building blocks are cleaved off, in the fluorescence of said nucleic acid molecules or/and said cleaved-off nucleotide building blocks.

The invention further relates to an apparatus for studying enzyme-substrate interactions, comprising
(a) a support comprising a multiplicity of enzyme molecules immobilized thereon.
(b) means for (i) delivering free substrate molecules carrying fluorescent labeling groups to said support, or (ii) generating free substrate molecules carrying fluorescent labeling groups on said support,
(c) a reaction space for reacting said substrate molecules with said immobilized enzyme molecules, and
(d) means for studying simultaneously a plurality of enzyme-substrate interactions of a plurality of enzyme or/and substrate molecules on the basis of the time-dependent change, caused during the enzymic reaction, in the fluorescence of said substrate molecules or/and the cleaved-off substrate parts or/and reaction products formed.

The invention further relates to an apparatus for sequencing nucleic acids comprising:
(a) a support comprising a multiplicity of nucleic acid-polymerising enzyme molecules immobilized thereon,
(b) means for providing (i) free nucleic acid molecules to which a primer molecule is bound and (ii) nucleotide building blocks carrying a fluorescent labeling group on the support,
(c) a reaction space for incorporating said nucleotide building blocks into said primer, and
(d) means for determining simultaneously the base sequence of a plurality of nucleic acid molecules on the basis of the time-dependent change, caused when nucleotide building blocks are incorporated, in the fluorescence of said extended primer molecule or/and of said nucleotide building blocks.

The apparatus is preferably a micro- or nanoscale structure suitable for determining single molecules, for example an at least partially transparent structure having channels or/and depressions. A preferred nano structure is described in PCT/EP02/02582.

The process of the invention and the apparatus of the invention may be employed, for example, in the analysis of genomes and transcriptomes or in differential analyses, for example studies regarding the difference in the genome or transcriptome of individual species or organisms within a species.

Furthermore, the figures below are intended to illustrate the present invention.

Figure 1:
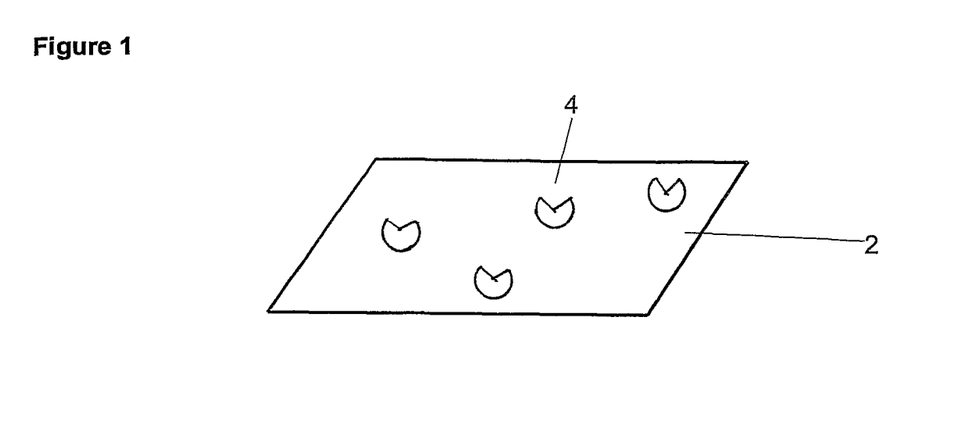

FIG. 1 is a diagrammatic representation of a support (2) of the invention having a multiplicity of enzyme molecules (4) immobilized thereto. A support having a surface area of from 1 to 2 cm$^2$ may contain up to 10$^6$ enzyme molecules, for example.

Figure 2:
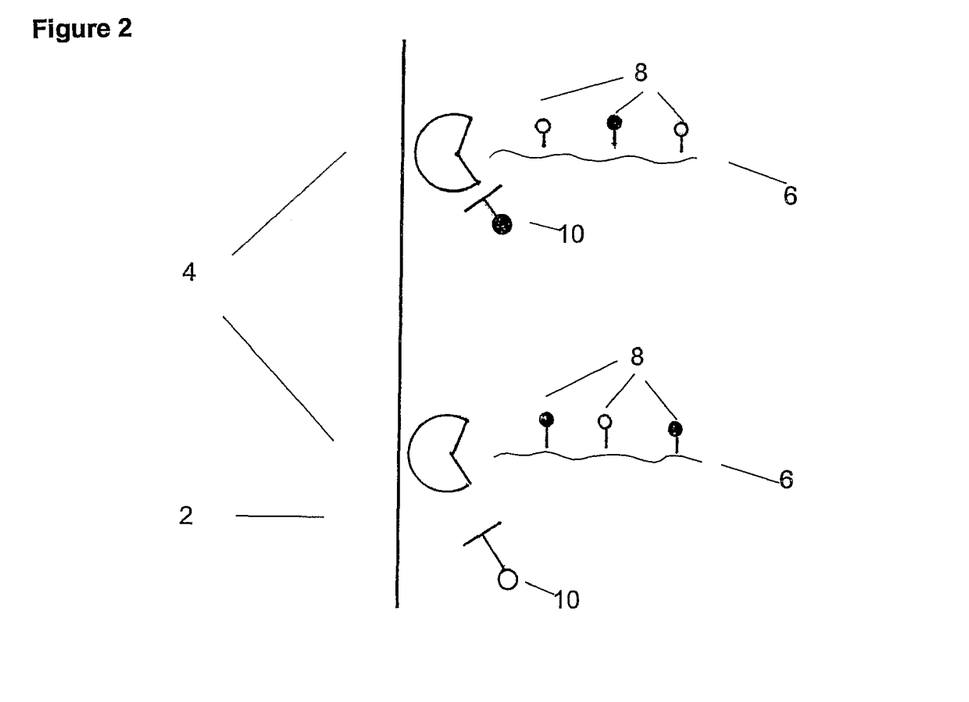

FIG. 2 depicts how the enzyme molecules (4) immobilized to the support (2) progressively cleave off individual nucleotide building blocks (10) from a free nucleic acid (6) having a plurality of fluorescent labeling groups (8). While the nucleotide building blocks incorporated into the nucleic acid strand exhibit only low fluorescence or no fluorescence at all, owing to quenching processes, said fluorescence increases after the removal by cleavage. Said increased fluorescence may be detected by means of a detector.

Figure 3A:
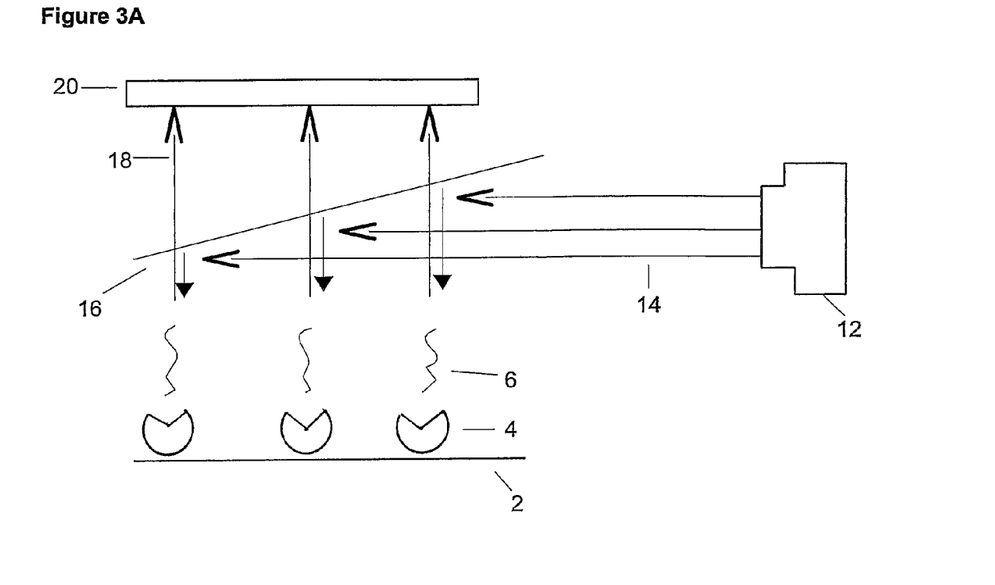

FIG. 3A depicts a first embodiment of the invention. Enzyme molecules (4) which degrade nucleic acid molecules (6) in the sample fluid are immobilized on the support (2). A laser (12) irradiates excitation light (14) through the sample fluid. Said excitation light (14) may be directed, for example by a diffraction-optical element (16), confocally to the positions of the individual immobilized enzyme molecules. The fluorescence emission light (18) emitted by the sample fluid is recorded by a detector matrix (20), for example a CCD or a CMOS camera.

Figure 3B:
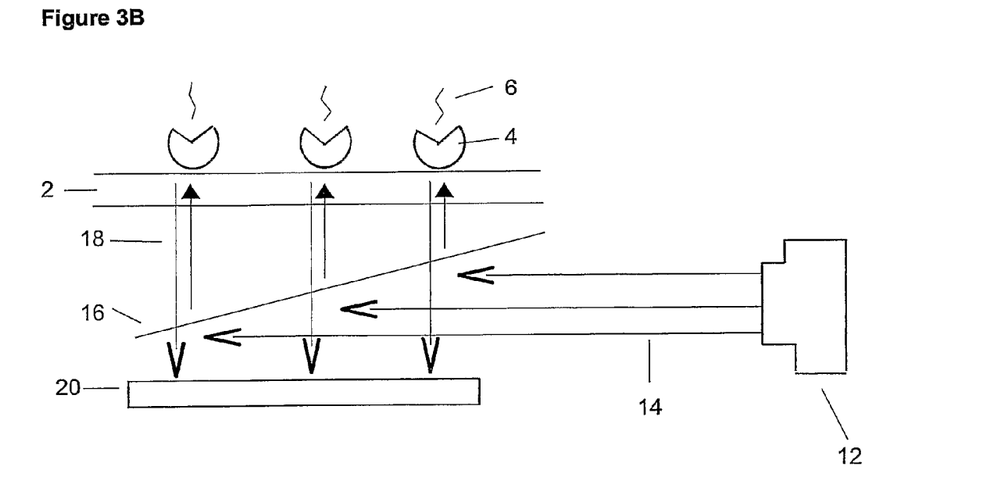

The embodiment depicted in FIG. 3B involves the enzyme molecules (4) being irradiated with excitation light (14), originating from the laser (12), through an optically transparent support (2). The emission light (18) which is likewise emitted through the support (2) is recorded by the detector matrix (20).

Figure 4:
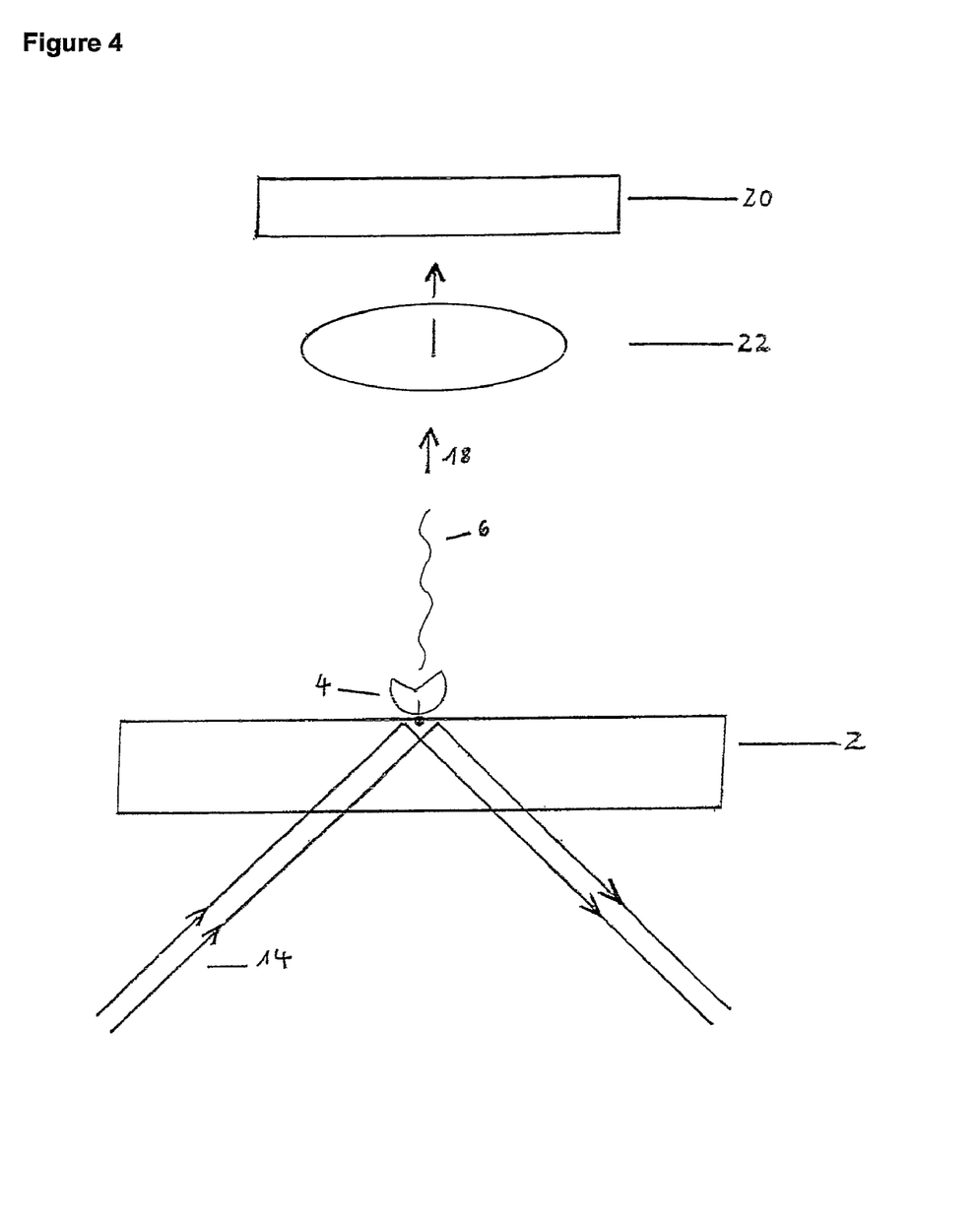

FIG. 4 depicts a further embodiment of the invention, wherein excitation light (14) of an expanded laser is irradiated into the optically transparent support (2) having enzyme molecules (4) immobilized thereto and nucleic acid molecules (6) to be sequenced and leaves the support (2) again after refraction at the support surface in the region of the immobilized enzyme molecules (4). In this manner, an evanescent excitation field is generated by which the fluorescently labeled nucleic acid molecules or nucleotide building blocks are excited and fluoresce. The emission light (18) is directed through an optical element (22) to a detector (20).

Figures 5, 6A:
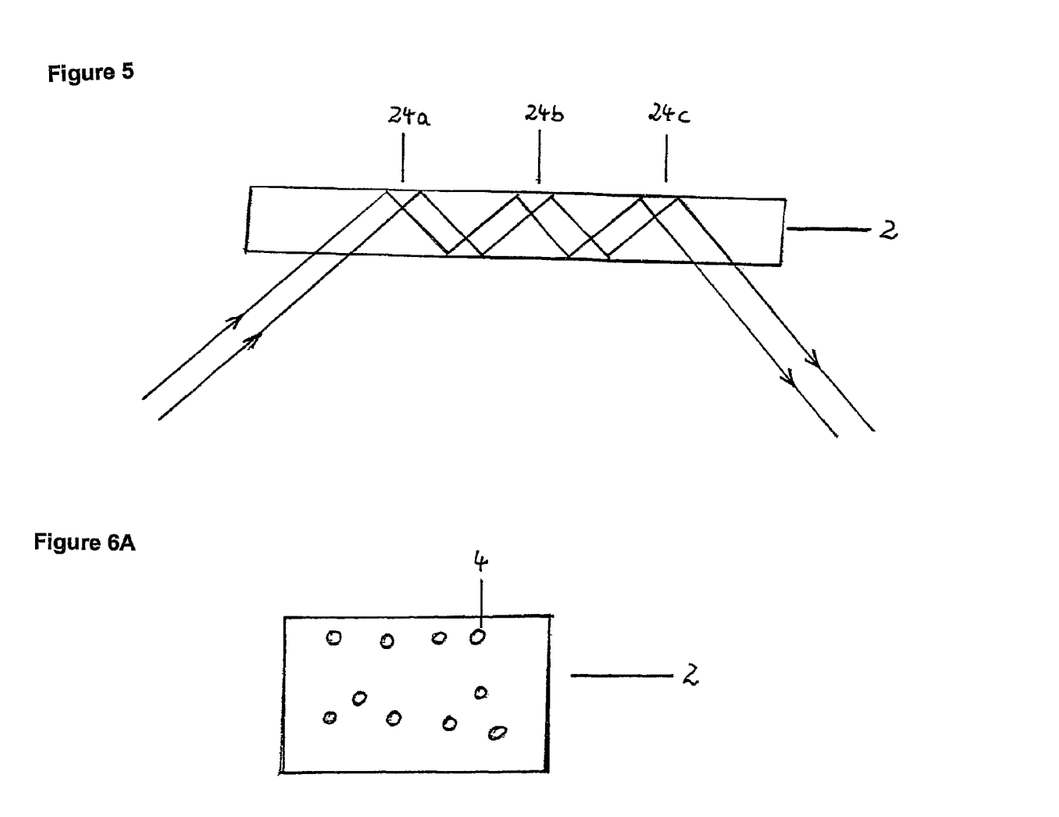

The embodiment depicted in FIG. 5 involves multiple refractions (24a, 24b, 24c) generating evanescent excitation fields in the optically transparent support (2). The evanescent excitation fields may be strip- or point-shaped, for example.

Alternatively, it is also possible to irradiate a plurality of laser light foci upon or into the support by using a diffractive optical element, as disclosed, for example, in DE 101 26 083.0.

Figure 6B:
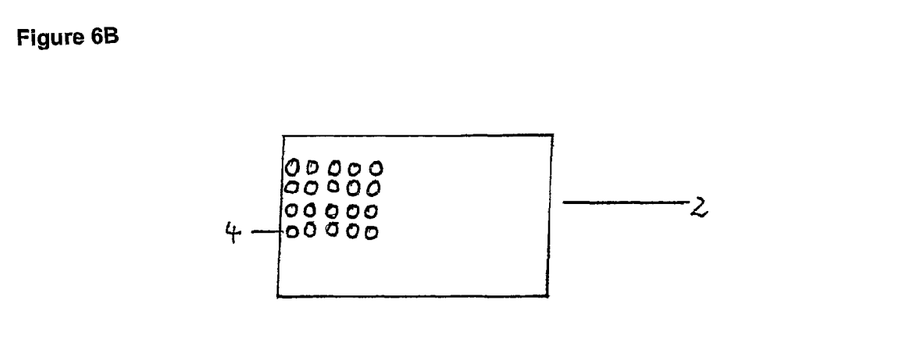

As shown in FIG. 6, the enzyme molecules immobilized on the support (2) may be arranged in a random or disordered manner on the support surface (FIG. 6A) or may be present in an ordered manner or on predefined structural areas (FIG. 6B).

Figure 7:
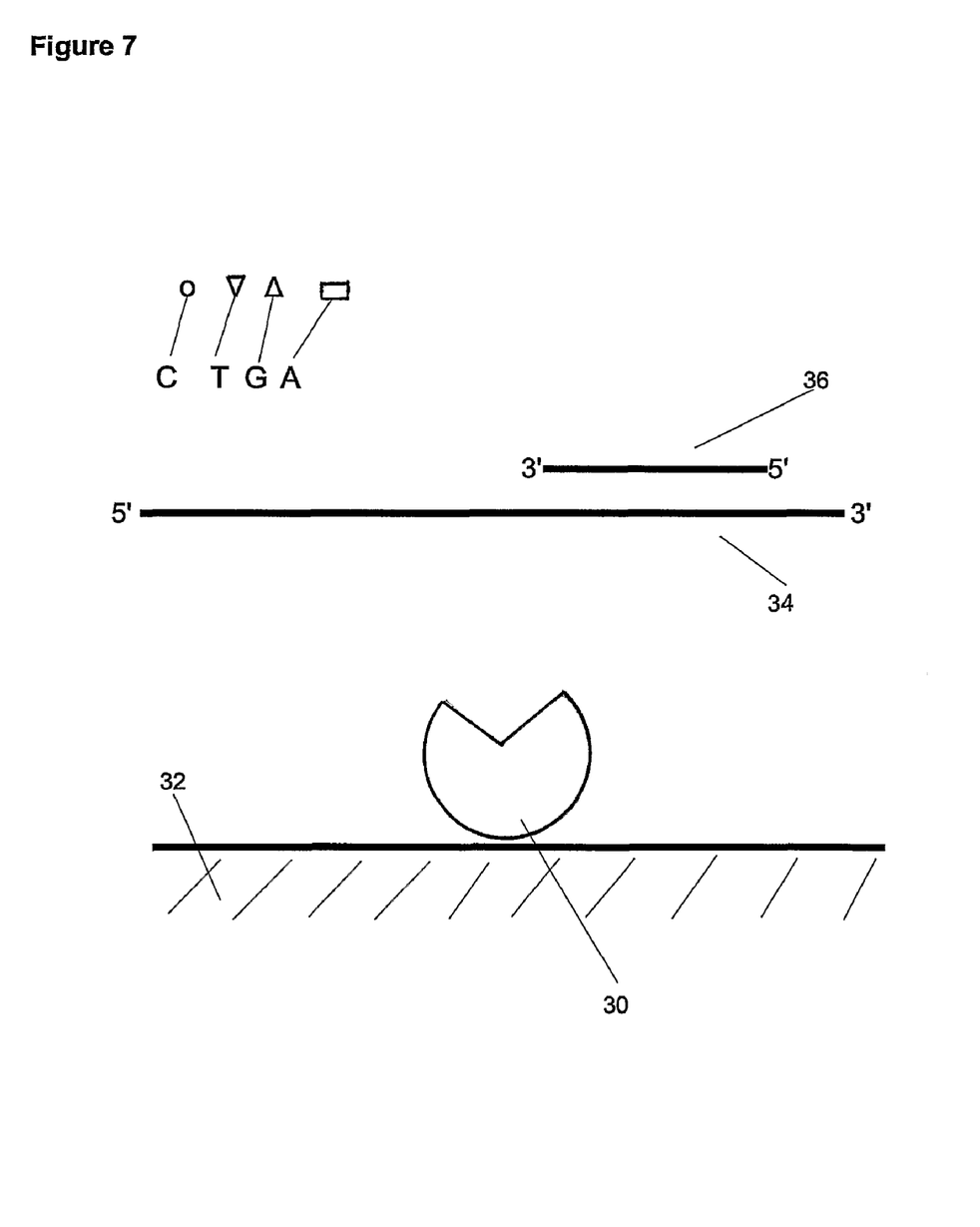

FIG. 7 depicts a further embodiment of the invention. This embodiment involves the use of a nucleic acid-polymerizing enzyme molecule (30) immobilized on a solid support (32). The immobilized enzyme (30) is contacted with a single-stranded nucleic acid template molecule (34) to which a primer molecule (36) having a 3'-end is bound. Further, nucleotide building blocks (A, G, T, C) each carrying a different fluorescence labeling group a present. Primer extension by incorporating the nucleotide building blocks generates a time-dependant change in the fluorescence which can be detected.

The invention claimed is:

1. A process for sequencing nucleic acids, comprising the steps of:
   providing a planar support having a multiplicity of nucleic acid-degrading enzyme molecules immobilized thereon, wherein the support is optically transparent at least in the region of the immobilized enzyme molecules,
   contacting said support with free nucleic acid molecules carrying a plurality of fluorescent labeling groups,
   progressively cleaving off individual nucleotide building blocks from said free nucleic acid molecules by said immobilized enzyme molecules, and
   simultaneously determining the base sequence of a plurality of nucleic acid molecules on the basis of the time-dependent change, caused when nucleotide building blocks are cleaved off, in the fluorescence of said nucleic acid molecules or/and of said cleaved-off nucleotide building blocks, wherein determining the base sequence comprises fluorescence excitation by lasers and wherein laser light is irradiated into the support and the formation of an evanescent excitation field is caused by internal reflection on the support surface in the region of the immobilized enzyme molecules.

2. The process as claimed in claim 1, wherein the support comprises at least one of a glass, a plastic, a quartz, a metal, a semimetal, a metal oxide or a composite thereof.

3. The process as claimed in claim 2, wherein determining the base sequence comprises multipoint fluorescence excitation by lasers.

4. The process as claimed in claim 1, wherein the enzyme molecules are selected from single-strand an double-strand exonucleases.

5. The process as claimed in claim 4, wherein determining the base sequence comprises multipoint fluorescence excitation by lasers.

6. The process as claimed in claim 1, wherein the enzyme molecules are selected from the group consisting of T7 DNA polymerase, *E.coli* exonuclease I and *E.coli* exonuclease III.

7. The process as claimed in claim 6, wherein determining the base sequence comprises multipoint fluorescence excitation by lasers.

8. The process as claimed in any of claim 1, wherein the enzyme molecules are immobilized on the support in a disordered manner.

9. The process as claimed in claim 8, wherein determining the base sequence comprises multipoint fluorescence excitation by lasers.

10. The process as claimed in claim 1, wherein the enzyme molecules are immobilized in predefined regions on the support in an ordered manner.

11. The process as claimed in claim 10, wherein determining the base sequence comprises multipoint fluorescence excitation by lasers.

12. The process as claimed in claim 1, wherein the nucleic acid molecules are labeled such that at least 50% of all nucleotide building blocks of one or more base types carry a fluorescent labeling group.

13. The process as claim in claim 12, wherein essentially all nucleotide building blocks of one base type carry a fluorescent labeling group.

14. The process as claimed in claim 1, wherein determining the base sequence comprises multipoint fluorescence excitation by lasers.

15. The process as claimed in claim 1, wherein determining the base sequence comprises detecting the fluorescence emission of a plurality of nucleic acid strands by means of a detection matrix.

16. The process as claimed in claim 15, wherein the detection matrix used is a CMOS camera, a CCD camera or an avalanche photodiode matrix.

17. The process as claimed in claim 1, wherein fluorescence excitation and fluorescence detection are carried out in parallel on all nucleic acid strands studied.

18. The process as claimed in claim 1, wherein fluorescence excitation and fluorescence detection are carried out in several steps, in each case on a portion of the nucleic acid strands studied.

19. The process as claimed in claim 1, wherein a convectional flow away from the support is generated during the determination.

20. The process as claimed in claim 1, wherein the fluorescent labeling groups are, at least partially, quenched when incorporated into the nucleic acid strands and the fluorescence intensity is increased after removal by cleavage.

21. The process as claimed in claim 1, wherein a support is provided which further has a multiplicity of nucleic acid-polymerizing enzyme molecules immobilized thereon and the free nucleic acid molecules carrying a plurality of fluorescent labeling groups are directly synthesized on the support.

22. The method of claim 1 performed with an apparatus comprising:
a planar support comprising a multiplicity of enzyme molecules immobilized thereon, wherein the support is optically transparent at least in the region of the immobilized enzyme molecules,
mean for (i) delivering free nucleic acid molecules carrying a plurality of fluorescent labeling groups to said support or (ii) generating free nucleic acid molecules carrying a plurality of fluorescent labeling groups on said support,
a reaction space for progressively cleaving off individual nucleotide building blocks from said nucleic acid molecules, and
means for determining simultaneously the base sequence of a plurality of nucleic acid molecules on the basis of the time-dependent change, caused when nucleotide building blocks are cleaved off, in the fluorescence of said nucleic acid molecules or/and said cleaved-off nucleotide building blocks comprising a laser for fluorescence excitation, by irradiating laser light into the support and casing the formation of an evanescent excitation field by internal reflection on the support surface in the region of the immobilized enzyme molecules.

23. An apparatus for sequencing nucleic acids, comprising
a planar support comprising a multiplicity of enzyme molecules immobilized thereon, wherein the support is optically transparent at least in the region of the immobilized enzyme molecules,
means for (i) delivering free nucleic acid molecules carrying a plurality of fluorescent labeling groups to said support or (ii) generating free nucleic acid molecules carrying a plurality of fluorescent labeling groups on said support,
a reaction space for progressively cleaving off individual nucleotide building blocks from said nucleic acid molecules, and
means for determining simultaneously the base sequence of a plurality of nucleic acid molecules on the basis of the time-dependent change, caused when nucleotide building blocks are cleaved off, in the fluorescence of said nucleic acid molecules or/and said cleaved-off nucleotide building blocks, comprising a laser for fluorescence excitation, by irradiating laser light into the support and casing the formation of an evanescent excitation field by internal reflection on the support surface in the region of the immobilized enzyme molecules.

24. The apparatus of claim 23, wherein the enzyme molecules are selected from nucleic acid degrading enzymes optionally in combination with nucleic acid polymerizing enzymes.

* * * * *